(12) United States Patent
Schneider et al.

(10) Patent No.: US 11,823,374 B2
(45) Date of Patent: Nov. 21, 2023

(54) MAGNIFIED HIGH RESOLUTION IMAGING AND TRACKING FOR MEDICAL USE

(71) Applicant: ELBIT SYSTEMS LTD., Haifa (IL)

(72) Inventors: Ron Schneider, Haifa (IL); Abraham Zeitouny, Haifa (IL)

(73) Assignee: Elbit Systems Ltd., Haifa (IL)

( * ) Notice: Subject to any disclaimer, the term of this patent is extended or adjusted under 35 U.S.C. 154(b) by 0 days.

(21) Appl. No.: 16/482,714

(22) PCT Filed: Jan. 31, 2018

(86) PCT No.: PCT/IL2018/050107
§ 371 (c)(1),
(2) Date: Aug. 1, 2019

(87) PCT Pub. No.: WO2018/142397
PCT Pub. Date: Aug. 9, 2018

(65) Prior Publication Data
US 2020/0242755 A1    Jul. 30, 2020

(30) Foreign Application Priority Data

Feb. 2, 2017 (IL) .......................................... 250432

(51) Int. Cl.
*G06T 7/00* (2017.01)
*G06T 7/70* (2017.01)
(Continued)

(52) U.S. Cl.
CPC ........ *G06T 7/0012* (2013.01); *G02B 27/0172* (2013.01); *G06F 9/542* (2013.01);
(Continued)

(58) Field of Classification Search
None
See application file for complete search history.

(56) References Cited

U.S. PATENT DOCUMENTS 5,766,016 A    6/1998  Sinclair et al.
5,836,869 A   11/1998  Kudo et al.
(Continued)

FOREIGN PATENT DOCUMENTS

CN    104918572    9/2015
CN    105916462    8/2016
(Continued)

OTHER PUBLICATIONS

JP 2004/177782 English computer generated translation; Inventor: Inomata M; Jun. 24, 2004 (Year: 2004).*
(Continued)

*Primary Examiner* — Nancy Bitar
(74) *Attorney, Agent, or Firm* — PEARL COHEN ZEDEK LATZER BARATZ LLP

(57) ABSTRACT

Imaging systems and methods are provided, which implement wide field imaging of a region for medical procedures and provide tracking of tools and tissues in the whole region while providing digitally magnified images of a portion of the captured region. Optical tracking may be implemented by stereoscopic imaging, and various elements may be optically tracked such as various markers and fiducials, as well as certain shapes and objects which are optically identifiable by image processing.

17 Claims, 5 Drawing Sheets

(51) Int. Cl.
*G06T 7/20* (2017.01)
*G06T 3/40* (2006.01)
*G02B 27/01* (2006.01)
*G06F 9/54* (2006.01)

(52) U.S. Cl.
CPC .............. *G06T 3/40* (2013.01); *G06T 7/20* (2013.01); *G06T 7/70* (2017.01); *G06T 2207/10048* (2013.01); *G06T 2207/30204* (2013.01)

(56) References Cited

U.S. PATENT DOCUMENTS

| | | | |
|---|---|---|---|
| 11,051,890 B2* | 7/2021 | Luks | A61B 1/0005 |
| 2009/0245600 A1 | 10/2009 | Hoffman et al. | |
| 2011/0301441 A1* | 12/2011 | Bandic | A61B 5/4875 |
| | | | 600/306 |
| 2012/0184846 A1* | 7/2012 | Izatt | A61B 3/132 |
| | | | 356/479 |
| 2012/0321759 A1* | 12/2012 | Marinkovich | A61B 5/442 |
| | | | 356/402 |
| 2013/0215515 A1* | 8/2013 | Kinoshita | G02B 30/56 |
| | | | 359/619 |
| 2015/0272694 A1 | 10/2015 | Charles | |
| 2016/0183779 A1* | 6/2016 | Ren | A61B 90/20 |
| | | | 351/246 |
| 2017/0027650 A1* | 2/2017 | Merck | A61B 1/00188 |
| 2017/0325907 A1* | 11/2017 | Maeda | H04N 13/139 |

FOREIGN PATENT DOCUMENTS

| | | | |
|---|---|---|---|
| CN | 106029000 | | 10/2016 |
| JP | 2008126063 A | | 6/2008 |
| JP | 2010142381 | | 7/2010 |
| JP | 2013248387 A | | 12/2013 |
| JP | 2014131552 A | | 7/2014 |
| WO | WO 2014/037953 | | 3/2014 |
| WO | WO 2015023990 | * | 2/2015 |
| WO | WO 2015/131088 | | 9/2015 |

OTHER PUBLICATIONS

Internarional Search report of PCT Application No. PCT/IL2018/050107, dated May 16, 2018.
Office Action for Chinese Patent Application No. 201880017265.9 dated Mar. 20, 2020.
Extended European Search Report for EP Patent Application No. 18748756.6, dated Nov. 4, 2020.
Office action for Japanese Patent Application No. 2019-541749, dated Dec. 14, 2021.
Office action for Japanese Patent Application No. 2019-541749, dated Sep. 27, 2022.

* cited by examiner

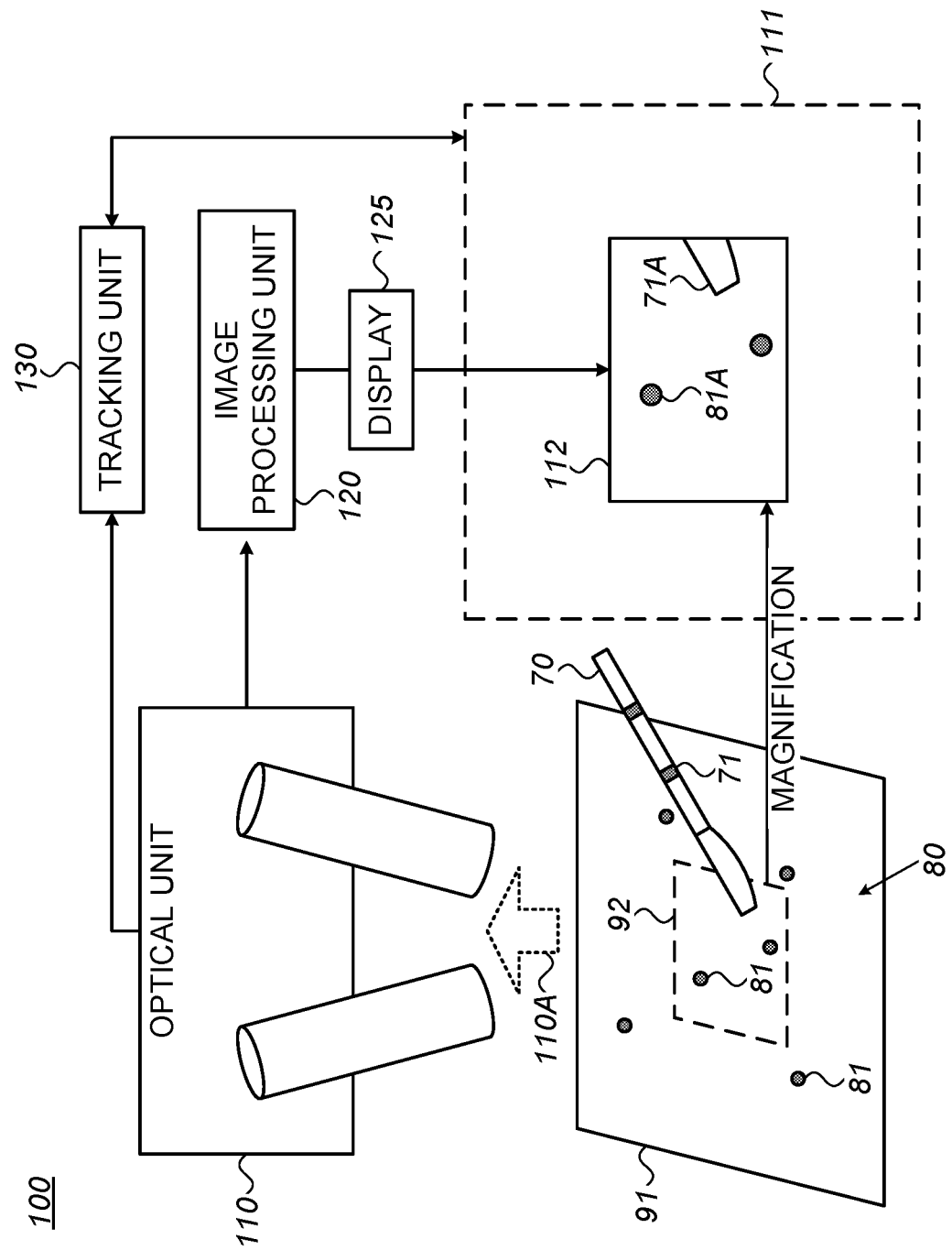

Narrow FOV cameras 115
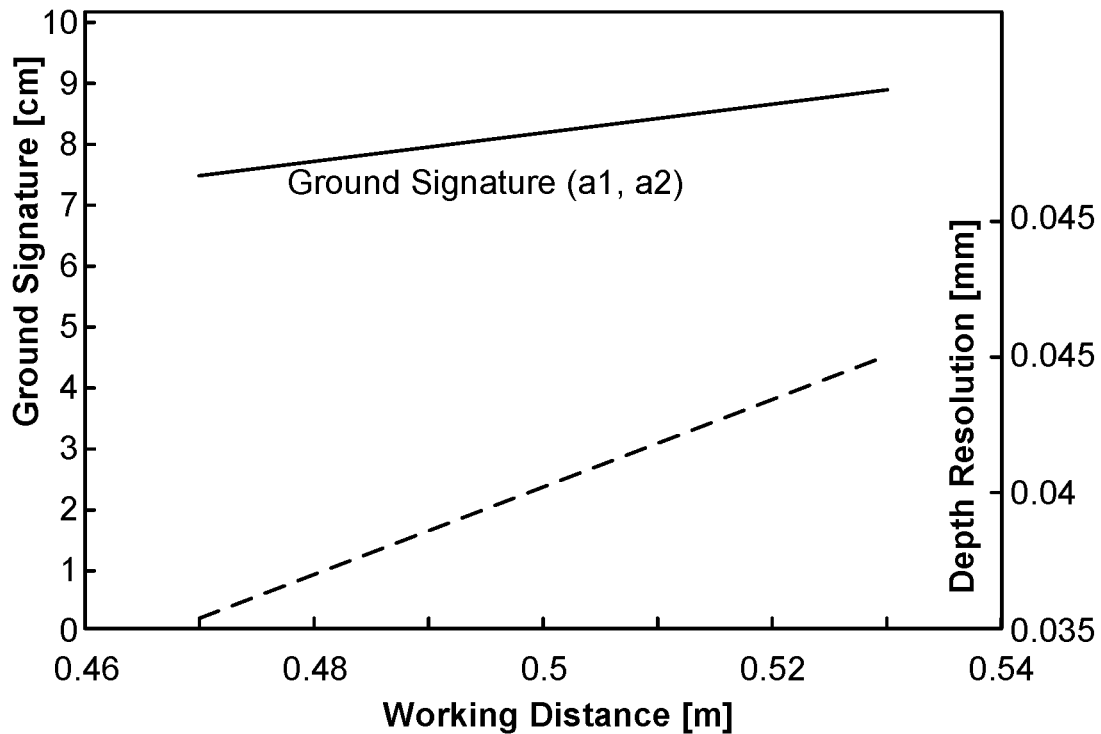
Wide FOV cameras 117
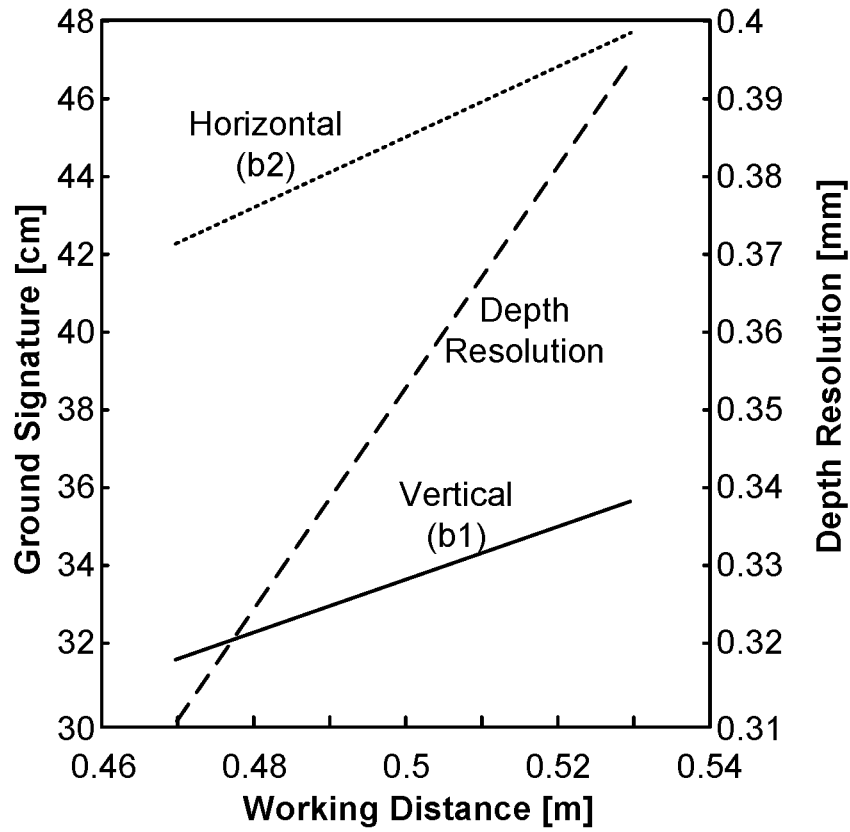
Figure 2B

MAGNIFIED HIGH RESOLUTION IMAGING AND TRACKING FOR MEDICAL USE

CROSS-REFERENCE TO RELATED APPLICATIONS

This application is a National Phase Application of PCT International Application No. PCT/IL2018/050107, International Filing Date Jan. 31, 2018, entitled: "MAGNIFIED HIGH RESOLUTION IMAGING AND TRACKING FOR MEDICAL USE", published on Aug. 9, 2018, under publication No. WO 2018/142397, which claims the priority of IL patent application No. IL250432, filed on Feb. 2, 2017, which is hereby incorporated by reference in its entirety

BACKGROUND OF THE INVENTION

1. Technical Field

The present invention relates to the field of wide field of view ultra-high resolution magnified digital imaging for medical purpose, and more particularly, for providing optical tracking on the basis of the ultra-high resolution images.

2. Discussion of Related Art

WIPO Publication No. 2014037953, which is incorporated herein by reference in its entirety, discloses a system for video capturing and displaying of surgeries, which may include: at least one digital image sensor optically coupled to one or more lenses and configured to capture a video sequence of a scene in a surgery; at least one interface configured to receive at least one region on interest (ROI) of the captured video sequence; an electronic display, selected so that at least one of the digital image sensors has a pixel resolution which is substantially greater than the pixel resolution of the electronic display; and a computer processor configured to: receive the at least one captured video sequence and the at least one received ROI and display over the at least one electronic display a portion of the captured video sequence based on the at least one selected ROI.

SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides a method comprising: capturing high resolution digital images in the visible spectral band/range of a treated region which is operated upon by at least one element such as a tool, displaying a digitally magnified area of the treated region, derived from the captured images, and tracking a position and orientation (P&O) of the at least one tool which is visible in the captured images, and the tracking mechanism of the tool is based on the captured images, wherein a resolution of the display is smaller than the captured high resolution images, and wherein the tracking is carried out at least outside the magnified area.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIGS. 1 and 2A are high level schematic block diagrams of an imaging system, according to some embodiments of the invention.

FIG. 2B illustrates a non-limiting example for performance of the optical unit, according to some embodiments of the invention.

DETAILED DESCRIPTION OF THE INVENTION

Figure 2A:
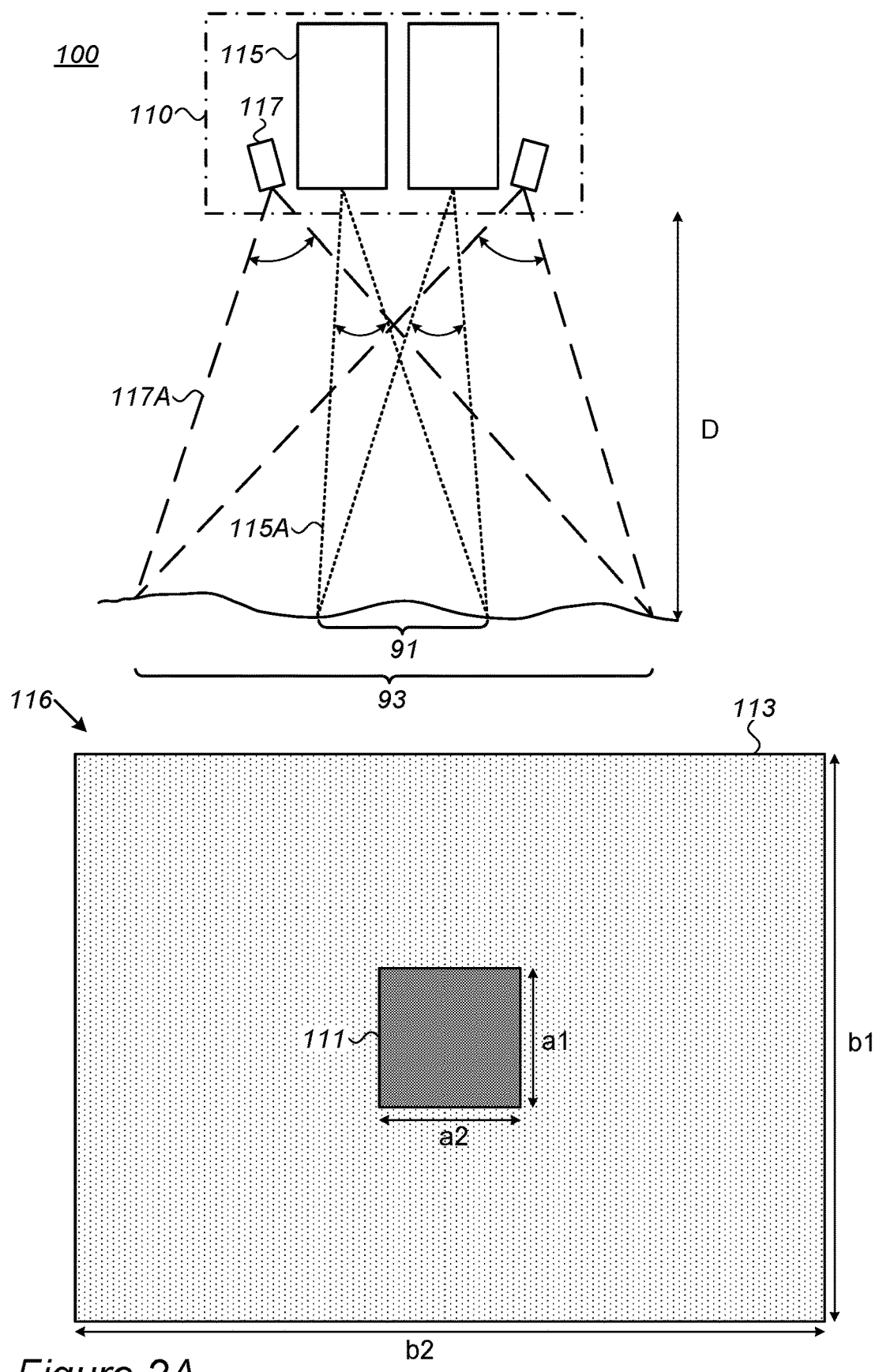

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein is for the purpose of description and should not be regarded as limiting.

Unless specifically stated otherwise, as apparent from the following discussions, it is appreciated that throughout the specification discussions utilizing terms such as "processing", "computing", "calculating", "determining", "enhancing" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices. Any of the disclosed modules or units may be at least partially implemented by a computer processor.

Embodiments of the present invention provide accurate, efficient and economical methods and mechanisms for tracking tools and tissues during an operation procedure by the imaging system used to digitally magnify an operation region. Imaging systems and methods are provided, which implement high resolution video imaging for medical procedures enabling digital magnification of the images by cropping a ROI (region of interest) smaller than the entire image FOV (field of view) and resizing it to fit a display, while at the same time tracking tool(s) and/or tissue(s) when these are visible in the whole treated region high resolution imaged FOV, even if the tool(s) and/or tissue(s) are not visible in the ROI. Optical tracking of tools and tissues may be implemented by stereoscopic imaging of the tool and tissue or by methods of structured light, time of flight or others. The tracked elements may be various markers and fiducial, as well as certain features, colors, shapes and objects which are optically identifiable in the images and are tracked using image processing techniques.

FIG. 1 is a high level schematic block diagram of an imaging system 100, according to some embodiments of the invention. Imaging system 100 comprises an optical unit 110 configured to capture digital images 110A in the visible spectral range of a treated region 91, which is operated upon by at least one tool 70 (as a non-limiting example for a tracked element, which may also comprise any object or tissue part); an image processing unit 120 configured to digitally magnify, from images 110A captured by optical unit 110, an area 92 (ROI) in treated region 91, and display a digitally magnified area 112 on a display 125; and a tracking unit 130 configured to track a position and orientation (P&O) of the at least one tool 70 in treated region 91 using captured images 110A.

The images are captured at high resolution, which is significantly higher than the resolution of display 125 which is used to display digitally magnified area 112. For example, captured high resolution may be 9,000·7,000 pixels (horizontal and vertical values), while the digitally magnified value may be smaller than 4,500·2,500 pixels (e.g., due to display size). For the display of the magnified resolution imaging system 100 may perform resizing to fit the display resolution. In certain embodiments, high resolution images may be captured at a resolution lower than 4,500·2,500 pixels and the display resolution may be at most 2,000·2,000 pixels. The ratio of display resolution to capturing resolution may be any ratio smaller than 1:1. The display may be any type of display, e.g., any type of screen or projection system, a head wearable display of any kind etc.

Image 112 is generated by using an ROI cropped out of the high resolution image(s) of region 91 (the full high resolution image is shown schematically as image 111 denoted by broken lines as its extent exceeds the size of the display and is hence not displayable at its full resolution). The tracking of tool 70 and any other elements such as objects, particles and possibly tissues in region 91 is carried out outside magnified area 92 (typically as well as inside magnified area 92) and provides tracking data beyond the displayed magnified area 112, i.e. tracking data that relates to area 111 which represents whole treated region 91. Therefore, using a single imaging sensor, both digital magnification and optical tracking are performed, based on the same captured images. For example, imaging system 100 may be configured to provide digitally magnified area 92 as being smaller than a third of the captured treated region 91, with the tracking carried out in the rest of region 91. The extended tracking by imaging system 100 may make additional tracking systems redundant and enhance tracking accuracy and simplicity by using same imaging system 100 for tracking as well.

Optical unit 110 and captured images 110A may be stereoscopic and tracking may be carried out according to stereoscopic 3D (three dimensional) image information. The digital images may comprise depth and/or 3D data derived from stereoscopic imaging, structured light imaging and/or time of flight imaging.

Tool(s) 70 may comprise fiducial(s) 71 and the P&O tracking may be carried out with respect to tool fiducial(s) 71. Alternatively or complementarily, the P&O tracking may be carried out with respect to various characteristics of tool 70 such as shape, color, specific sub-elements etc. Treated region 91 may comprise tissue markers (or possibly fiducial(s)) 81 and tracking unit 130 may be further configured to track tissue markers 81 in treated region 91 using captured images 110A. Alternatively or complementarily, the P&O tracking may be carried out with respect to various characteristics of treated region 91 such as shape, color, specific sub-elements etc.

Fiducial(s) 71 and markers 81 may be of any kind used in the art. As the tracking is based on optical imaging, shapes of tissue parts and/or tool parts may be used for the tracking without need for fiducial(s) 71 and/or markers 81, or using fewer fiducial(s) 71 and/or markers 81 than needed when tracking is based on these alone. For example, specific tissue features (e.g., blood vessels, certain tissue types, tissue growths etc.) and/or specific tool features (e.g., blade or handle parts) may be identified as having a shape which is distinct enough to enable efficient optical tracking, and may be used to implement the tissue and/or tool tracking. Tracking unit 130 may be configured to select and optimize tracking target(s) and provide corresponding data.

Imaging system 100 may be configured to provide data concerning the tracked P&O of tool(s) 70 such as distances and relative positions between tools 70 and/or tool parts and specific tissue, other tools 70, surgeon's fingers etc. Imaging system 100 may be configured to provide alerts and/or guidance corresponding to certain situations such as proximity of a tool's blade to certain tissue which is not meant to be cut in a specified procedure, an orientation of an ablative laser as tool 70 which may cause unwanted damage to tissue, etc. Imaging system 100 may be configured to provide guidance data for aiding a surgeon to reach desired tissues and to drive the tool through a desired path. Imaging system 100 may be configured to provide alerts and/or guidance concerning specified spatial relation(s) between the tracked P&O of tool(s) 70 and treated region 91.

Imaging system 100 may further comprise additional lower resolution camera(s) having a wider field of view, which are configured to capture images of a region that encloses region 91 to provide rough tracking data outside and around the working FOV of the magnification system.

FIG. 2A is a high level schematic block diagram of an imaging system 100, according to some embodiments of the invention. Optical unit 110 may comprise multiple cameras 115, 117 for capturing image 110A, such as high resolution camera(s) 115 (with respective FOVs 115A) which image region 91 (and may enlarge ROIs 92 within region 91) and wide-FOV camera(s) 117 (with respective FOVs 117A which is wider than FOVs 115A) covering a larger region 93—providing a compound image 116 which is composed of image 111 captured by high resolution camera(s) 115 and image 113 captured by the wider FOV camera/s 117. The overlap region between images 111, 113 may be used to calibrate image parameters and/or be processed to provide a continuous transition between images 111, 113 in image 116.

Images 111, 113 are indicated schematically to have dimensions a1·a2 and b1·b2 respectively, for example, a1 and a2 may be between 1-10 cm and b1 and b2 may be between 10-100 cm. The typical working distance of optical unit 110, denoted by D, may ranges between 10-100 cm.

For example, FIG. 2B illustrates a non-limiting example for performance of optical unit 110, according to some embodiments of the invention. The used dimensions are D around 50 cm, a1 and a2 around 8 cm, b1 around 35 cm and b2 around 45 cm. FIG. 2B illustrates changes in ground signatures (e.g., a1, a2, b1 and b2) and depth accuracies (in the non-limiting example, in the range of 0.3-0.4 mm for wide FOV cameras 117 and in the range of 0.035-0.045 mm for narrow FOV cameras 115).

In certain embodiments, tracking (e.g., by any 3D tracking method) may be implemented with respect to region 93 as well, and the overlap region between images 111, 113 may be used to handover and/or calibrate the tracking between tracking unit 130 and trackers operating in region 93. In certain embodiments, tracking unit 130 may be further configured to track region 93 as well through wide FOV camera(s) 117.

For example, high resolution camera(s) 115 may be part of a video microscope and wide-FOV camera(s) 117 may operate in the visible range and/or in the near infrared. Image processing unit 120 may be configured to display images 111 of high resolution camera(s) 115 on display 125, possibly with data overlaid on it, such as data from CT (computer tomography), MRI (magnetic resonance imaging) etc. In certain embodiments, any data augmented in relation to any feature in area 116 may be projected on display 125. The information on what part of the data to overlay and in what coordinates may be provided according to tracking data by tracking unit 130. For example, 2D or 3D MRI images of an imaged tumor or spine may be overlaid on image 116 acquired by wide and narrow FOV camera(s) 117, 115, respectively, at a high positional accuracy using the tracking data by tracking unit 130. In some cases markers/fiducial 81 may be outside of area 91, and inside area 93. In such cases, camera(s) 117 may be configured to capture images of markers 81 for tracking of the area and/or tissues, while camera(s) 115 may be configured to capture images of tool 70 or markers 71 for tracking of tool 70.

In some embodiments, system 100 may be configured to use the tracking data from using camera(s) 115 and/or camera(s) 117. In the area in which tracking data from both sources is available, the tracking data may be improved by comparing the data from the sources, e.g., by interpolation or any other mixing method, to improve the tracking. In certain embodiments, the more accurate data (or data from one source) may be used for the tracking while and the less accurate data (or data from the second source) may be used to decrease noises in the tracker results, double check the tracking results for safety and/or used for any other purpose. In the transition between areas 116 and 111, tracking data may be interpolated using the data from camera(s) 115 and camera(s) 117, possibly with a decreasing weight for camera(s) 117 as the tracking area is going toward the center of area 111. In certain embodiments, the weight for camera(s) 117 may be set to zero before reaching the center of area 111.

Figure 3:
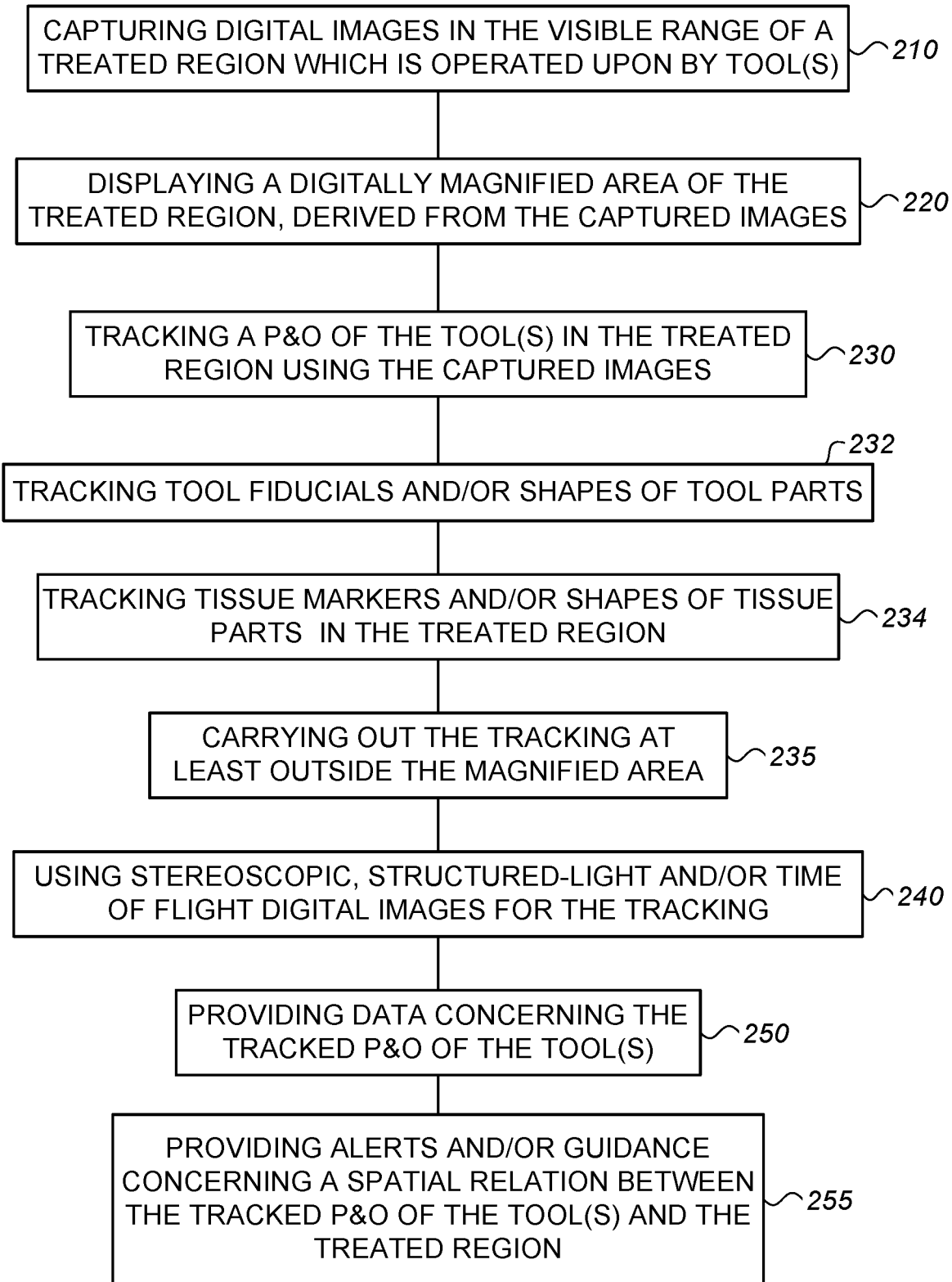
FIG. 3 is a high level flowchart illustrating a method, according to some embodiments of the invention.
Figure 3:
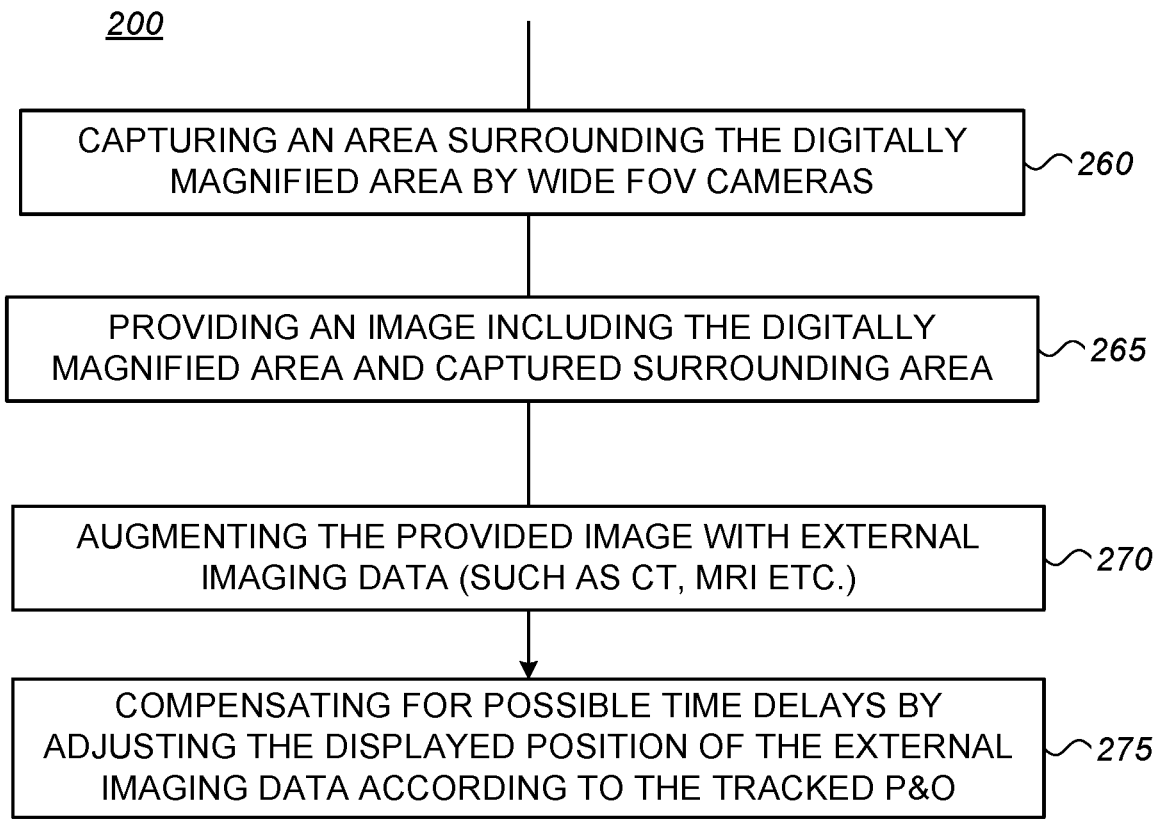

FIG. 3 is a high level flowchart illustrating a method 200, according to some embodiments of the invention. The method stages may be carried out with respect to system 100 described above, which may optionally be configured to implement method 200. Method 200 may be at least partially implemented by at least one computer processor. Certain embodiments comprise computer program products comprising a computer readable storage medium having computer readable program embodied therewith and configured to carry out of the relevant stages of method 200. Method 200 may comprise stages for operating imaging system 100, such as any of the following stages, irrespective of their order.

Method 200 may comprise capturing high resolution digital images in the visible spectral range of a treated region which is operated upon by at least one tool (stage 210), displaying a digitally magnified area of the treated region, derived from the captured images (stage 220), and tracking a position and orientation (P&O) of the at least one tool in the treated region using the captured images (stage 230), wherein the tracking is carried out at least outside the magnified area (stage 235). The resolution of the display is smaller than the capturing high resolution, for example, the digitally magnified area may be smaller than the captured treated region by any factor (e.g., 1.5, 2, 3, 5 and higher) and tracking 230 may be carried out over the whole treated region.

Method 200 may comprise tracking tool fiducial(s) and/or shapes of tool parts using the captured images (stage 232). Method 200 may comprise tracking tissue markers and/or shapes of tissue parts in the treated region (stage 234).

Method 200 may comprise using stereoscopic or structured light digital images for the tracking (stage 240). Any type of depth data or 3D information, derived e.g., from stereoscopic imaging, structured light imaging and/or time of flight imaging, may be incorporated in the digital images.

Method 200 may comprise providing of data concerning the tracked P&O of the tool(s) (stage 250) and possible providing alerts and/or guidance concerning a spatial relation between the tracked P&O of the tool(s) and the treated region (stage 255).

Method 200 may comprise capturing an area surrounding the digitally magnified area by wide FOV (field of view) cameras (stage 260) and providing an image including the digitally magnified area and captured surrounding area (stage 265). Method 200 may further comprise augmenting the provided image with external imaging data (stage 270) and optionally compensating for time delays with respect to the external imaging data by adjusting a displayed position of the external imaging data according to the tracked P&O (stage 275).

Imaging system 100 and method 200 may be implemented in systems and methods such as described in WIPO Publication No. 2014/037953 and may incorporate elements described in WIPO Publication No. 201403795.

Aspects of the present invention are described above with reference to flowchart illustrations and/or portion diagrams of methods, apparatus (systems) and computer program products according to embodiments of the invention. It will be understood that each portion of the flowchart illustrations and/or portion diagrams, and combinations of portions in the flowchart illustrations and/or portion diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or portion diagram or portions thereof.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or portion diagram portion or portions thereof.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or portion diagram portion or portions thereof.

The aforementioned flowchart and diagrams illustrate the architecture, functionality, and operation of possible implementations of systems, methods and computer program products according to various embodiments of the present invention. In this regard, each portion in the flowchart or portion diagrams may represent a module, segment, or portion of code, which comprises one or more executable instructions for implementing the specified logical function(s).

It should also be noted that, in some alternative implementations, the functions noted in the portion may occur out of the order noted in the figures. For example, two portions shown in succession may, in fact, be executed substantially concurrently, or the portions may sometimes be executed in the reverse order, depending upon the functionality involved. It will also be noted that each portion of the portion diagrams and/or flowchart illustration, and combinations of portions in the portion diagrams and/or flowchart illustration, can be implemented by special purpose hardware-based systems that perform the specified functions or acts, or combinations of special purpose hardware and computer instructions.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A method of determining a position and orientation of a tool relative to a part of a tissue in a treated region, the method comprising:
    capturing high resolution digital images of the treated region, which is operated upon by the tool, using a first set of cameras of an optical unit, the first set of cameras operating in a visible spectral range;
    displaying, over a display, a digitally magnified region of interest of the treated region, derived from the captured high resolution digital images; capturing tracking data, using at least one of a second set of cameras of the optical unit, the second set of cameras having a wide field-of-view and operating in the infrared spectral range, wherein the tracking data are from outside and around the magnified region of interest; and wherein the tracking data consist of images of the tool or tool fiducial/s for tracking of the tool; determining a first position and orientation of the part of the tissue relative to the optical unit based on depth and/or 3D data derived from the high-resolution digital images;
    determining a second position and orientation of the tool relative to the optical unit based on the tracking data determining the position and orientation of the tool relative to the part of the tissue based on the first position and orientation and the second position and orientation; and displaying a digitally magnified area of the treated region, wherein a resolution of the display is lower than the captured high resolution digital images.

2. The method of claim 1, wherein the displaying is carried out on a head wearable display.

3. The method of claim 1, wherein at least one of said tracking is carried out according to depth and/or 3D data derived from the digital images.

4. The method of claim 1, wherein the at least one tool comprises at least one fiducial and/or marker, and wherein the tracking is based on said at least one fiducial and/or marker.

5. The method of claim 1, further comprising providing alerts or guidance concerning the relative position.

6. The method of claim 1, wherein the treated region comprises tissue features, wherein said tracking a part of a tissue in said treated region is based on tracking the tissue features in the treated region using the captured images.

7. The method according to claim 1, wherein the tracking of the part of the tissue is carried out according to stereoscopic 3D (three dimensional) image information.

8. The method according to claim 1, wherein the tracking the tool is carried out by carried out according to stereoscopic 3D (three dimensional) image information.

9. The method according to claim 1, wherein the second set of cameras have a lower resolution relative to the first set of cameras.

10. An imaging system for determining a position and orientation of a tool relative to a part of a tissue in a treated region, the imaging system comprising: an optical unit configured to capture high resolution digital images of the treated region, which is operated upon by the tool, using a first set of cameras of an optical unit, the first set of cameras operating in a visible spectral range; a display configured to display a digitally magnified region of interest of the treated region, derived from the captured high resolution digital images; tracking unit configured to: capture tracking data, using at least one of a second set of cameras of the optical unit, the second set of cameras having a wide field-of-view and operating in the infrared spectral range, wherein the tracking data are from outside and around the magnified region of interest; and wherein the tracking data consist of images of the tool or tool fiducial/s for tracking of the tool; determine a first position and orientation of the part of the tissue relative to the optical unit based on depth and/or 3D data derived from the high-resolution digital images;

determine a second position and orientation of the tool relative to the optical unit based on the tracking data;

and determine the position and orientation of the tool relative to the part of the tissue based on the first position and orientation and the second position and orientation, wherein the display is further configured to display a digitally magnified area of the treated region, wherein a resolution of the display is lower than the captured high resolution digital images.

11. The imaging system of claim 10, wherein the display is a head wearable display.

12. The imaging system of claim 10, wherein the optical unit and the captured images are stereoscopic, and wherein said step of tracking is carried out according to stereoscopic three dimensional (3D) image information.

13. The imaging system of claim 10, wherein the tool comprises at least one fiducial and/or marker and the position tracking is carried out based on the at least one tool fiducial tool.

14. The imaging system of claim 10, wherein the treated region comprises tissue features, and wherein the tracking unit is further configured to track the tissue features in the treated region using the captured images.

15. The imaging system of claim 10, further configured to provide alerts or guidance concerning a spatial relation between the tracked position of tool and the part of the tissue in said treated region.

16. The imaging system of claim 10, wherein the optical unit further comprises wide FOV cameras configured to capture an area surrounding the area, and wherein the image processing unit is further configured to provide an image including the digitally magnified area and the captured surrounding area.

17. The imaging system according to claim 10, wherein the second set of cameras have a lower resolution relative to the first set of cameras.

* * * * *